US010057732B2

(12) United States Patent
Soomro

(10) Patent No.: US 10,057,732 B2
(45) Date of Patent: Aug. 21, 2018

(54) CONTENT SPECIFIC RING TONES FOR CLINICIAN ALERTS

(71) Applicant: KONINKLIJKE PHILIPS N.V., Eindhoven (NL)

(72) Inventor: Amjad Soomro, Hopewell Junction, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 70 days.

(21) Appl. No.: 14/349,676

(22) PCT Filed: Oct. 5, 2012

(86) PCT No.: PCT/IB2012/055353
§ 371 (c)(1),
(2) Date: Apr. 4, 2014

(87) PCT Pub. No.: WO2013/057615
PCT Pub. Date: Apr. 25, 2013

(65) Prior Publication Data
US 2014/0248858 A1 Sep. 4, 2014

Related U.S. Application Data

(60) Provisional application No. 61/548,242, filed on Oct. 18, 2011.

(51) Int. Cl.
H04W 4/12 (2009.01)
G06F 19/00 (2018.01)
(Continued)

(52) U.S. Cl.
CPC .......... *H04W 4/12* (2013.01); *G06F 19/3418* (2013.01); *G08B 3/1041* (2013.01); *G16H 40/63* (2018.01); *G08B 7/06* (2013.01)

(58) Field of Classification Search
CPC ....................................................... H04M 3/42
(Continued)

(56) References Cited

U.S. PATENT DOCUMENTS 7,433,465 B2 * 10/2008 Casey ................. G06F 19/3418
348/E5.102
7,619,584 B2 * 11/2009 Wolf ..................... G06F 3/0489
345/1.2
(Continued)

FOREIGN PATENT DOCUMENTS

WO 2004/070557 8/2004
WO 2005010796 A2 2/2005
(Continued)

*Primary Examiner* — Kamran Afshar
*Assistant Examiner* — Majid Syed

(57) ABSTRACT

A system for alterting heathcare practitioners (20) includes a plurality of receiving devices (10), and a sending station (30). Each of the plurality of receiving device is associated with a corresponding healthcare practitioner. The receiving device (10) includes a user alerting device (120), a receiver (110), and circuitry (160). The user alerting device (120) alerts the practitioner to a received message with one of a plurality of types of alerts. The receiver (110) receives the incoming messages. The circuitry (160) causes the user alerting device to alert the practitioner to an incoming message with one of the plurality of types of alerts. The sending station (30) sends the messages carrying healthcare information of one of a plurality of preselected types of healthcare significants to a selected one or more of the receiving devices, each message corresponding to a selected one of the types of alerts, such that the receiving device alerts the practitioner to receiving the message with the selected type of alerts.

20 Claims, 9 Drawing Sheets

(51) Int. Cl.
*G08B 3/10* (2006.01)
*G16H 40/63* (2018.01)
*G08B 7/06* (2006.01)

(58) Field of Classification Search
USPC .................. 379/373.01–373.04; 455/567
See application file for complete search history.

(56) References Cited

U.S. PATENT DOCUMENTS

| | | | |
|---|---|---|---|
| 8,406,407 B2 * | 3/2013 | Opaluch | H04M 3/02 |
| | | | 379/207.16 |
| 8,560,632 B2 | 10/2013 | Kamga | |
| 2004/0006492 A1 | 1/2004 | Watanabe | |
| 2006/0045252 A1 * | 3/2006 | Gorti | H04M 19/041 |
| | | | 379/201.02 |
| 2008/0021741 A1 | 1/2008 | Holla et al. | |
| 2009/0150172 A1 * | 6/2009 | Duffey-Rosenstein | G06F 19/327 |
| | | | 705/2 |
| 2009/0204858 A1 | 8/2009 | Kawaba | |
| 2009/0326339 A1 * | 12/2009 | Horvitz | G06Q 10/00 |
| | | | 600/301 |
| 2012/0108917 A1 * | 5/2012 | Libbus | A61B 5/0006 |
| | | | 600/301 |

FOREIGN PATENT DOCUMENTS

| | | | |
|---|---|---|---|
| WO | 2006050176 A2 | 5/2006 | |
| WO | 2006127791 A2 | 11/2006 | |

\* cited by examiner

| Alert | Ringtone | Vibrate | Light | Expected Action |
|---|---|---|---|---|
| 1 | pattern 1 | none | none | contact office |
| 2 | pattern 5 | pattern A | none | review incoming patient alert |
| 3 | pattern 9 | pattern A | pattern Z3 | urgent contact radiology desk |
| 4 | pattern 2 | pattern C | pattern X5 | urgent contact patient |
| 5 | pattern 9 | none | pattern Z3 | urgent patient critical alert |
| 6 | none | pattern X | none | lab result to review |
| 7 | pattern 3 | none | pattern F2 | contact pharmacy regarding prescription |
| 8 | none | pattern C | pattern Z3 | review patient discharge order |
| 9 | pattern 1 | pattern C | pattern X5 | urgent contact office, patient in distress |

Figure 5

CONTENT SPECIFIC RING TONES FOR CLINICIAN ALERTS

CROSS REFERENCE TO RELATED APPLICATIONS

This application is a national filing of PCT application Serial No. PCT/IB2012/055353, filed Oct. 5, 2012, published as WO 2013/057615 A1 on Apr. 25, 2013, which claims the benefit of U.S. provisional application Ser. No. 61/548,242 filed Oct. 18, 2011, which is incorporated herein by reference.

The present application relates to clinical systems, hospitals systems, mobile devices, and specifically to alerts delivered to clinicians on their mobile devices.

Clinicians are mobile and are increasingly equipped with devices that enable practicing healthcare in a mobile environment. The mobile environment includes connectivity to the Internet, to voice communications, to hospital systems, and to clinical systems. A typical clinician carries a smartphone or other mobile device such as a tablet computer, cell phone, or the like. In the course of providing care, a clinician may use phone communications, email, instant messaging, and system access through a web browser. System access may involve reviewing lab results or other diagnostic information, creating orders or prescriptions, scheduling, and reacting to a variety of different events that arise during the day. Because clinicians are mobile, changes in schedule, new results, or new events are increasingly sent as messages.

The messages to a clinician arise from a variety of sources depending upon the practice specialty and/or healthcare role. Depending upon the size of the healthcare practice, facilities used, and specialty some roles are combined while others are separated. One or more schedulers handle new appointments, regularly scheduled patient visits, lab tests for patients, follow-up appointments, emergency appointments, and administrative appointments such as healthcare facility administration, pharmaceutical agent visits, or other vendors. Healthcare practitioners also react to events such as receipt of lab results, patient calls, system monitors, patient monitors, etc. These events are often communicated to a clinician as an electronic message such as voice, text, or email depending upon the nature, urgency, or expected response.

Messages communicated to a clinician cannot all be communicated in the same manner or the clinician would likely be overwhelmed. Clinicians attempt to balance review of new events and changes with care delivery by establishing filters and allowing more interruptions than are needed. One method of filtering is to hire staff at an office which reviews messages, and only forwards messages according to the nature, urgency, and expected response from the clinician at that point in time. This reduces the traffic of messages to the clinician, but moves the decision making of the messages away from the clinician. This also involves the added expense of staff which are not always present in a 24 hour day.

Another approach is to enable faster review of messages with shorter text messages. The healthcare practitioner still visually reviews each message, but less time is spent on each message. Combinations of establishing filters, shortening messages, and visually reviewing each message are the usual result. The healthcare practitioner interrupts their workflow to review all messages, or defers reviewing all messages to continue current care.

Hospital and clinical systems often include various types of patient monitors. Thresholds are established and systems are programmed to automatically send messages to clinicians. These appear as messages from the same source, a system monitor. Frequently, a clinician receives a message knowing only that it is from a monitor and must review the message to determine the nature, urgency, and expected response.

Current technology allows a clinician only a limited means to differentiate the nature, urgency, and expected response of a message when received before reviewing the content of the message. A ringtone of a mobile device or smartphone is used to alert a clinician that a message has been received from a particular source such as an office, a lab, an ICU, etc., but does not allow any alerts which differentiate based on the message content.

Alerts which differentiate the nature, urgency, and expected response to a message would be advantageous to allow a clinician to decide how to best integrate the review of the message into their personal workflow. This depends upon balancing the nature, urgency, and expected response of the current task with that suggested in the message alert which is best decided by the healthcare practitioner.

The present application provides a new and improved method and system for contect specific alerts to clinicians which overcomes the above-reference problems and others.

Modern phones have the ability to generate a selected ringtone for each of a plurality of designated callers. In one example of the present concept, the medical institution has a plurality of outgoing telephone numbers, each corresponding to a different type of alert, e.g. the urgency of a medical situation. When it is necessary to alert a practitioner to a medical issue, the outgoing cellphone voice call or text message is sent from the telephone number that corresponds to the urgency of the medical situation and the type of alert. The practitioners phone then rings with a ringtone that indicates the type of alert. Rather than the ringtone, a display opens, or a vibration can be used to indicate the alert type. For email messages Internet Protocol (IP) addresses can be used in the same way.

Future mobile devices may have a plurality of telephone numbers or IP addresses. Each telephone number or IP address is associated with a ringtone or the like which indicates a corresponding one of a plurality of alert types. The message concerning the medical situation is sent to the telephone number or IP address corresponding to the alert type.

In accordance with one aspect, a system for alterting heathcare practitioners includes a plurality of receiving devices, and a sending station. Each of the plurality of receiving device is associated with a corresponding healthcare practitioner. The receiving device includes a user alerting device, a receiver, and circuitry. The user alerting device alerts the practitioner to a received message with one of a plurality of types of alerts. The receiver receives the incoming messages. The circuitry causes the user alerting device to alert the practitioner to an incoming message with one of the plurality of types of alerts. The sending station sends the messages carrying healthcare information of one of a plurality of preselected types of healthcare significants to a selected one or more of the receiving devices, each message corresponding to a selected one of the types of alerts, such that the receiving device alerts the practitioner to receiving the message with the selected type of alerts.

In accordance with another aspect, a system for alterting heathcare practitioners is provided. A patient monitor monitors physiological parameters and outputs a message to one of the practitioners indicative of the monitored physiological condition and a healthcare significance of the monitored physiological condition. A sending station associates an alert type which corresponds to the healthcare significance associated with the message and the associated type of alert to a receiving device of one of the practitioners. The receiving device alerts the practitioner with the type of alert which corresponds to the medical significance of the message.

In accordance with another aspect, a method for alerting healthcare practitioners sends a message to a selected one or more receiving devices, the message carrying healthcare information with one or a plurality of types of preselected healthcare significances. With one of the receiving devices, the healthcare message is received and the receipt responded to by performing a type of alert corresponding to the one of the types of healthcare significances of the message carried healthcare information.

In accordance with another aspect, a method for alerting sends a message to a selected one or more receiving devices, the message carrying information with one or a plurality of types of preselected significances. With one of the receiving devices, receiving the message and alerting a person associated with the receiving device by performing a type of alert corresponding to the one of the types of preselected significances.

One advantage is that alerts can be used to indicate message content.

Another advantage is that ringtone alerts provide hands free information dissemination to a healthcare practitioner.

Another advantage is that alerts can be standardized for healthcare, a healthcare service provider, healthcare facility, or a healthcare practitioner.

Another advantage is that alerts can be customized for a healthcare practitioner.

Another advantage is that alerts can accommodate multiple originators of messages.

Another advantage resides in indicating the nature, urgency, and/or expected response to a healthcare practitioner before the message is read.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 4A:
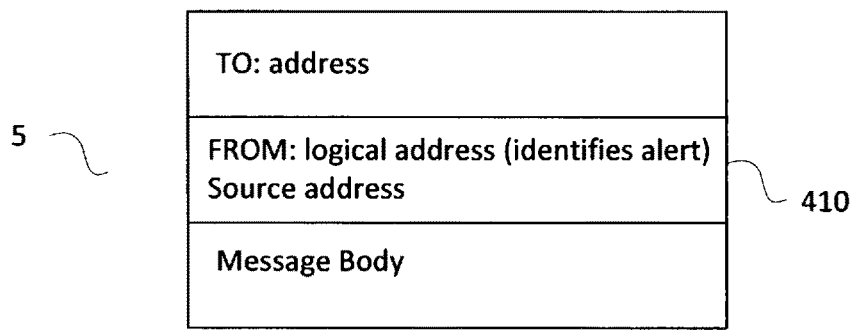
Figure 4B:
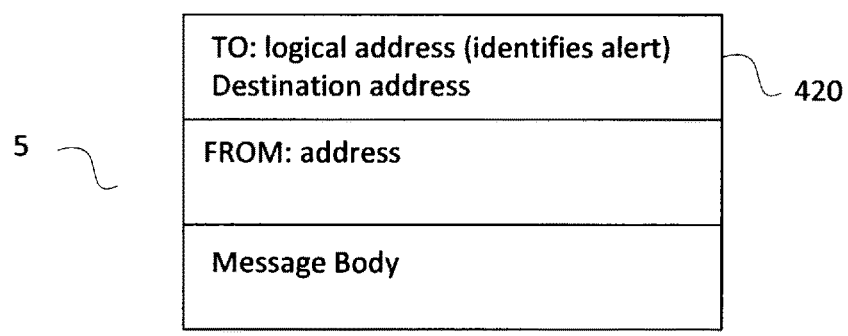
Figure 4C:
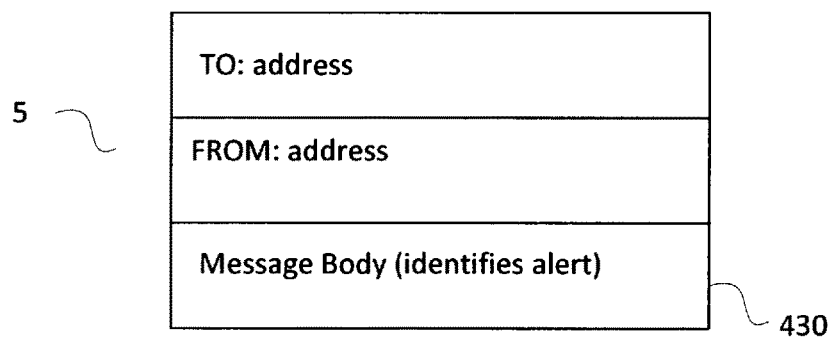

FIGS. 4A, 4B, and 4C are diagrams of message formats which trigger various clinician alerts.

FIG. 5 is an example table showing possible alert configurations manifested at the destination device.

Figure 6:
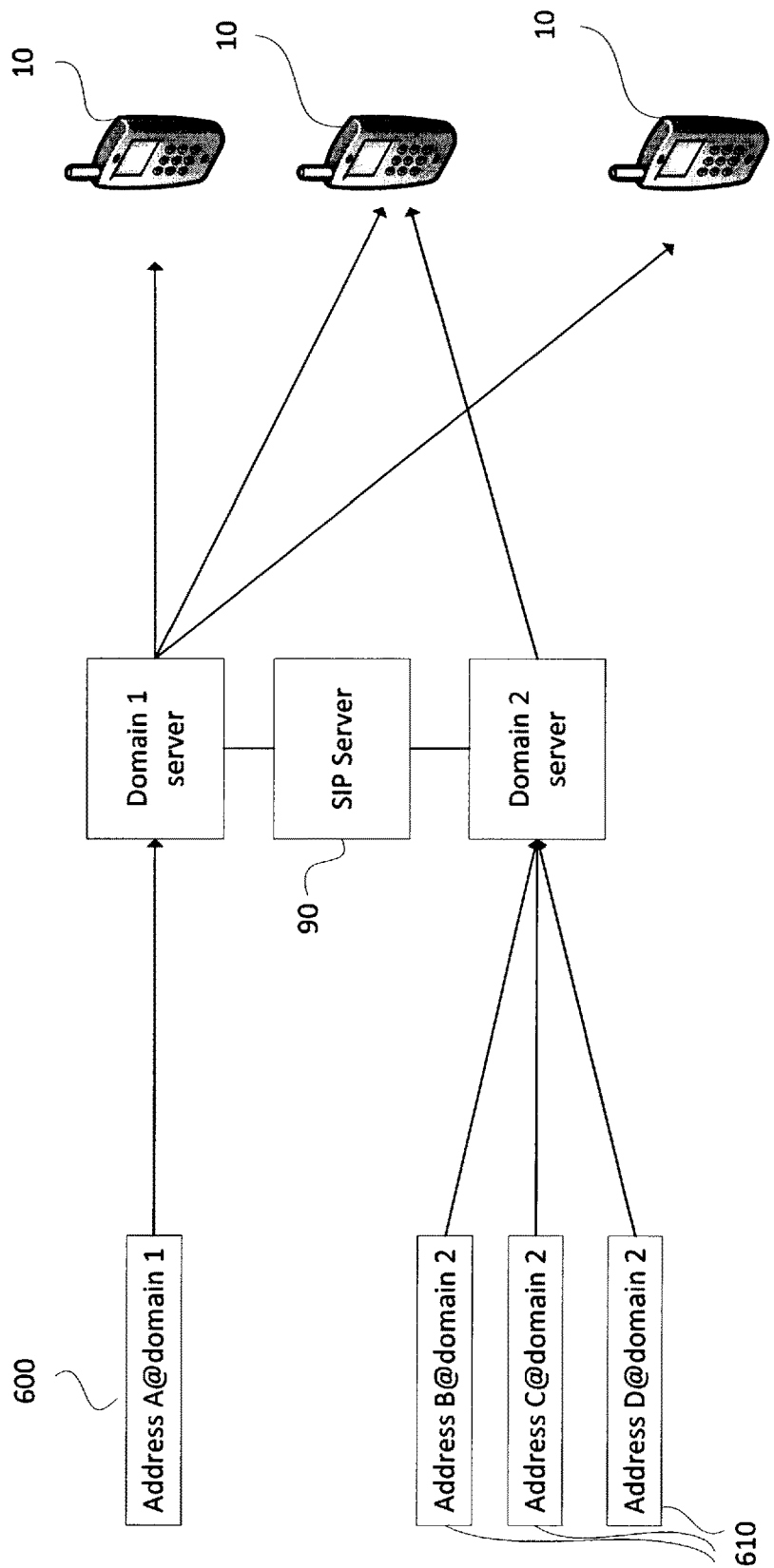

FIG. 6 is a diagram which illustrates the possible 1–n device destinations and the m–1 sources using a SIP protocol.

Figure 7:
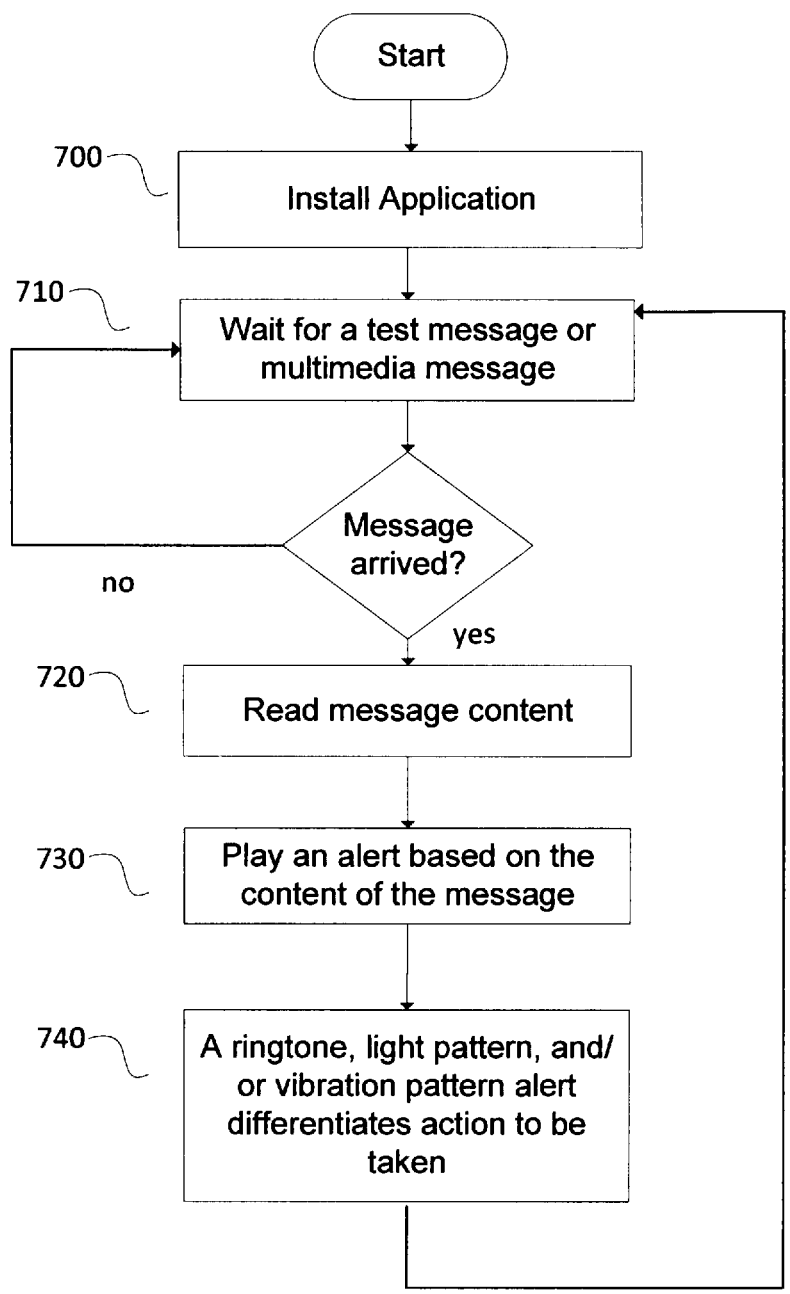

FIG. 7 is a flowchart of an embodiment which triggers alerts based on the content of a message body.

Figure 8:
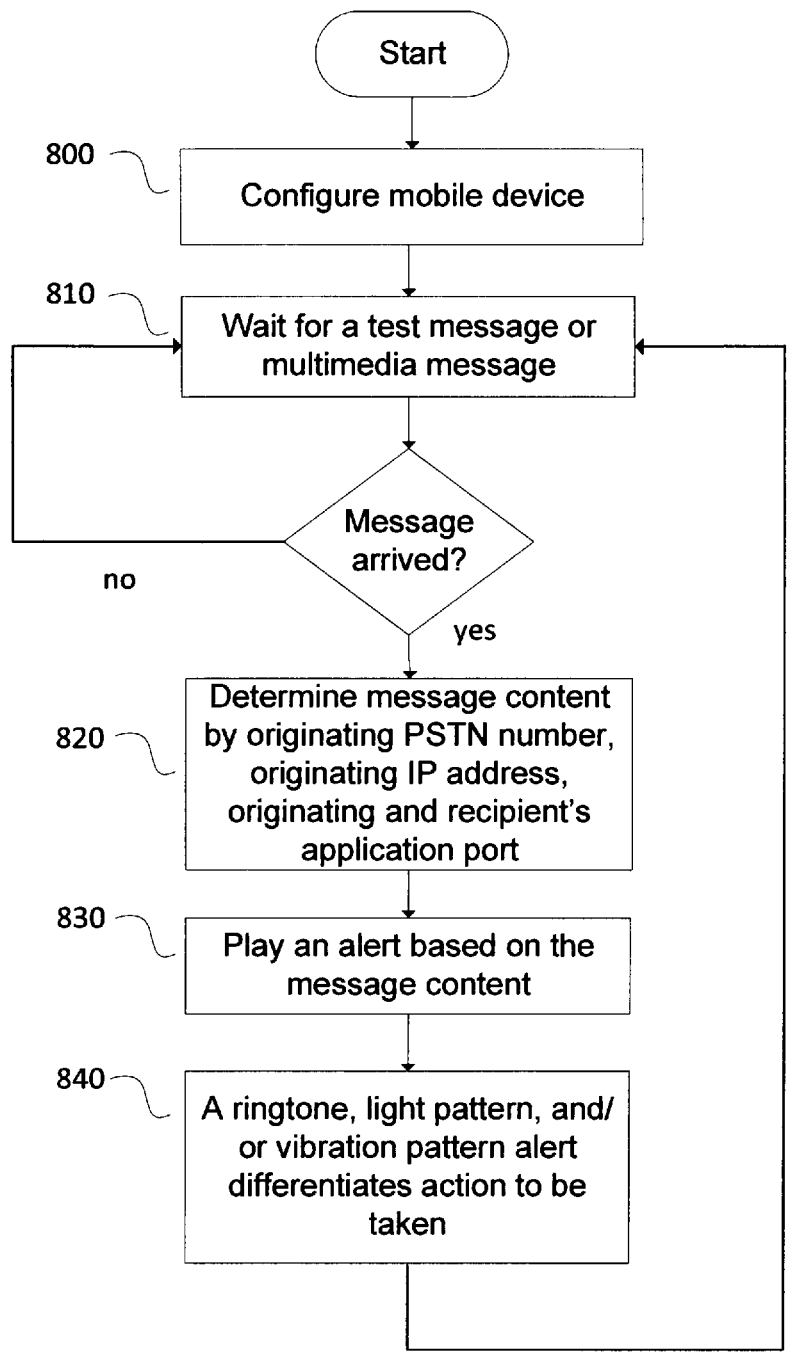

FIG. 8 is a flowchart of an embodiment which triggers alerts based on the message content reflected by the source and/or destination address.

Figure 9A:
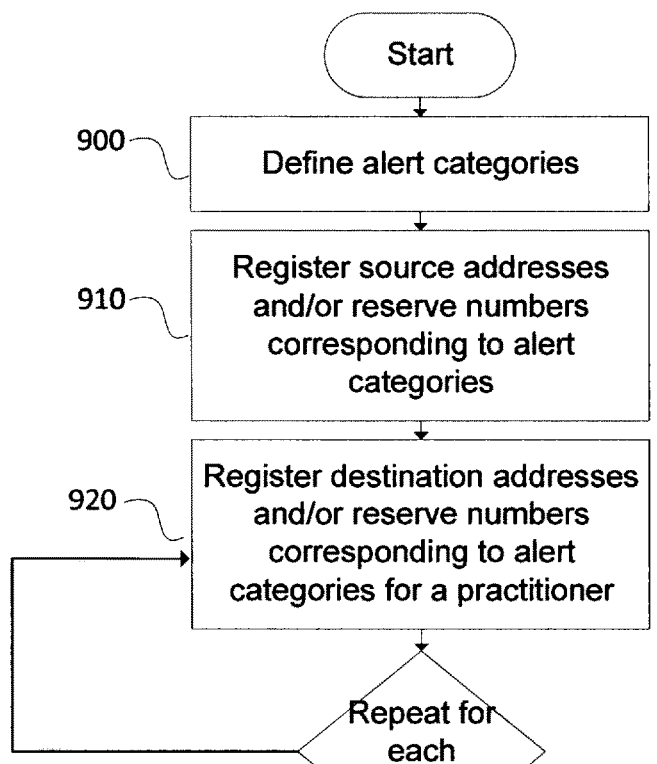
Figure 9B:
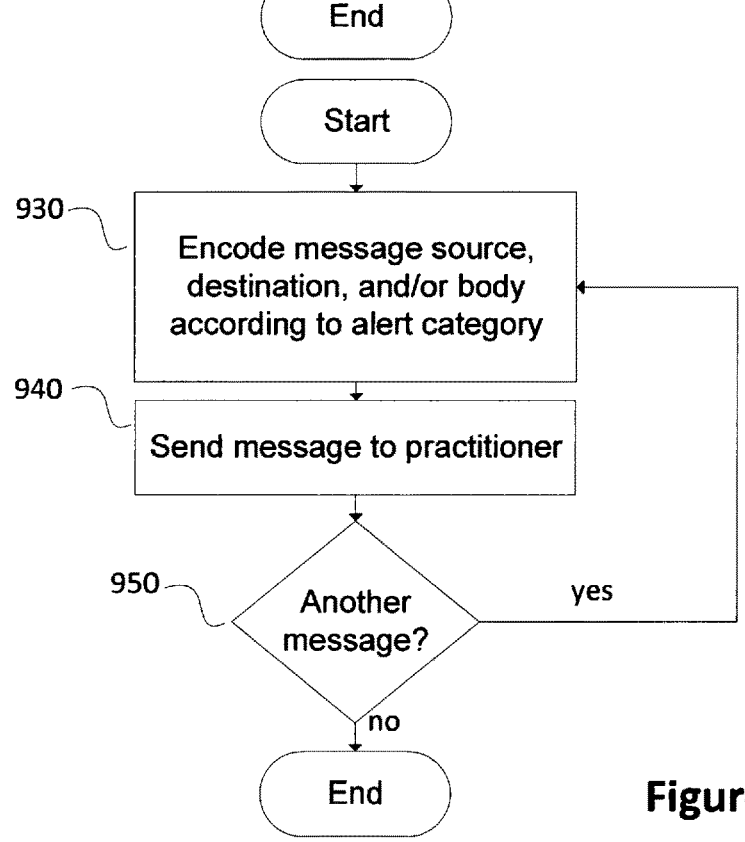

FIGS. 9A and 9B are flowcharts of the set-up and the sending of messages respectively in one embodiment.

Figure 1:
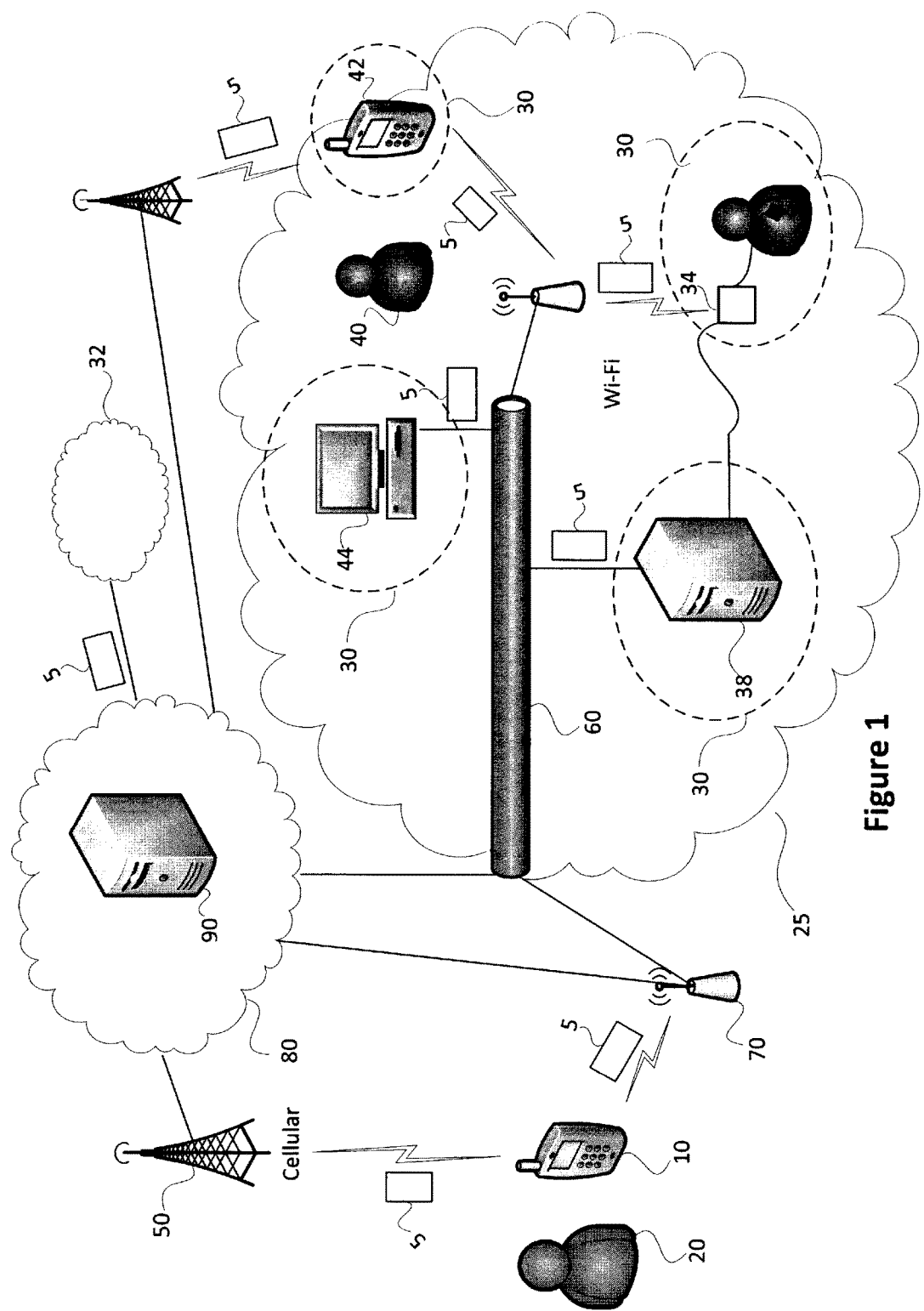
FIG. 1 is a diagram illustrating the environment in which alerts are sent in an embodiment to a destination clinicians with an expanded view of a receiving device.

With reference to FIG. 1, messages 5 arrive at a receiving device 10, such as a cellphone, smartphone, PDA, or the like, of a clinician 20 from a variety of sources, a variety of mechanisms, and in a variety of message formats. Alerts on the destination clinician's 20 smartphone or other receiving device indicate the nature, urgency, and/or expected response to a message 5 or a message content. Sources of messages include organizations 25 such hospitals or healthcare facilities. Message originators send messages from a sending station 30 such as a server, desktop, laptop, smartphone, monitoring device or the like. Message originators include system authored sources such as patient monitors 34, systems 38 for scheduling, hospital administrative, lab, radiology, in-patient and the like, out-patient systems 32, and other clinician or healthcare practitioners 40 through voice communication 42 and/or system communication 44. Connectivity is maintained through cellular systems 50, or public system telephone networks (PSTN), wired and wireless networks such as ethernet 60 and wi-fi 70, Internet 80, and the like and interconnected combinations thereof.

Messages are delivered as voice, email, text, and instant messages and include text, voice and other multi-media formats. Message technology uses Internet Protocols (IP), short message system (SMS), PSTN protocols, and the session initiation protocol (SIP). SIP is an Internet Engineering Task Force (IETF) developed signaling protocol. SIP permits registration of multiple logical addresses using a SIP configured server 90 which map to an address. A logical address can include information indicating the nature, urgency, and/or expected response of messages which use that logical address.

A set of IP addresses, SIP logical addresses, port numbers, PSTN numbers, and/or combinations are used to send and/or receive messages. Where addresses previously indicated a device or a person, address combinations now indicate both a person or device and a nature, urgency, and/or expected response. The messages 5 are categorized to use an address combination representing an agreed upon message category between the healthcare practitioner 20 and the organization or organizations 25. Each organization can define message categories and associated expected responses. Default configurations can be provided to the practitioners. The practitioner can combine or separate configurations of multiple organizations. Alerts which are triggered on the receiving device 10 and correspond to a message category are configured on the receiving device 10.

Figure 2:
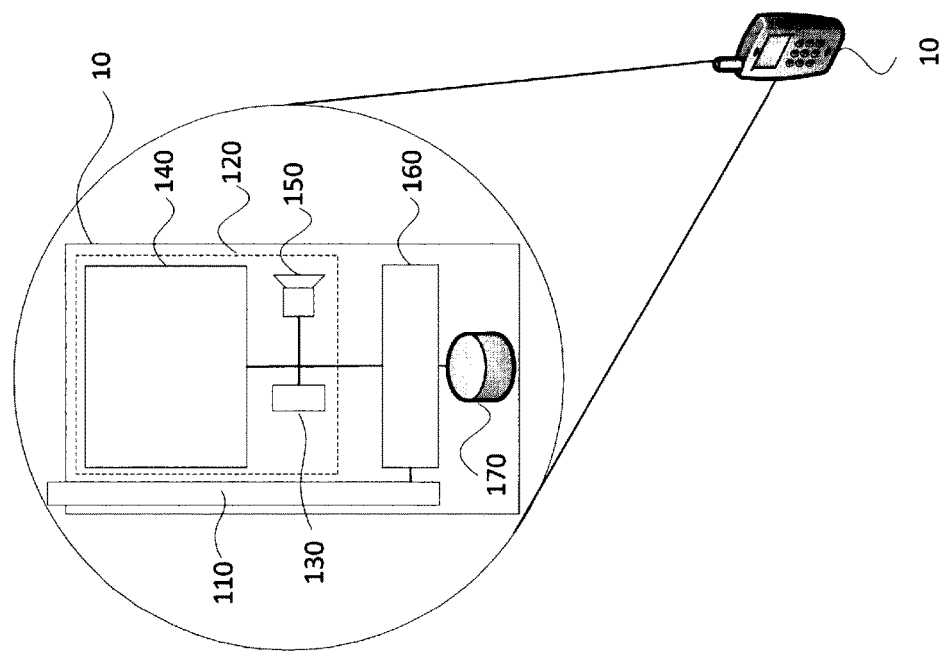
FIG. 2 is a diagram of one embodiment of a receiving device.

The alerts configured on the receiving device 10 include manual entry and/or downloads. The alerts can be specific to the heathcare practitioner 20, the healthcare provider, and/or the healthcare facility 25, or generalized to the healthcare. For example, an immediate life threatening emergency, commonly known as a code blue may have an alert which is an alarm ringtone, and a blue flashing light on the smartphone display. With reference to FIG. 2, the receiving device 10 in one embodiment includes a receiver 110 which receives the incoming message 5. The receiver 110 receives from either wireless connection of the Wi-Fi 70 or the PSTN 50. A circuitry 160 processes the received message from the receiver and identifies the alert indicated by the message 5. Using a stored configuration in the receiving device memory 170, the circuitry 160 activates various components in an alerting device 120.

The alerting device 120 includes a vibrating device 130, an audio output device 150, and an optical display device 140. The vibrating device 130 when activated causes a vibration pattern to the receiving device 10 according to the alert pattern configured. The audio output device 150 sounds or plays the ringtone pattern configured for the alert indicated by the received message 5. The optical output display 140 used for normal input/output display functions of the device 10 displays the color and/or flashing pattern triggered by the alert indicated by the received message 5.

Figure 3:
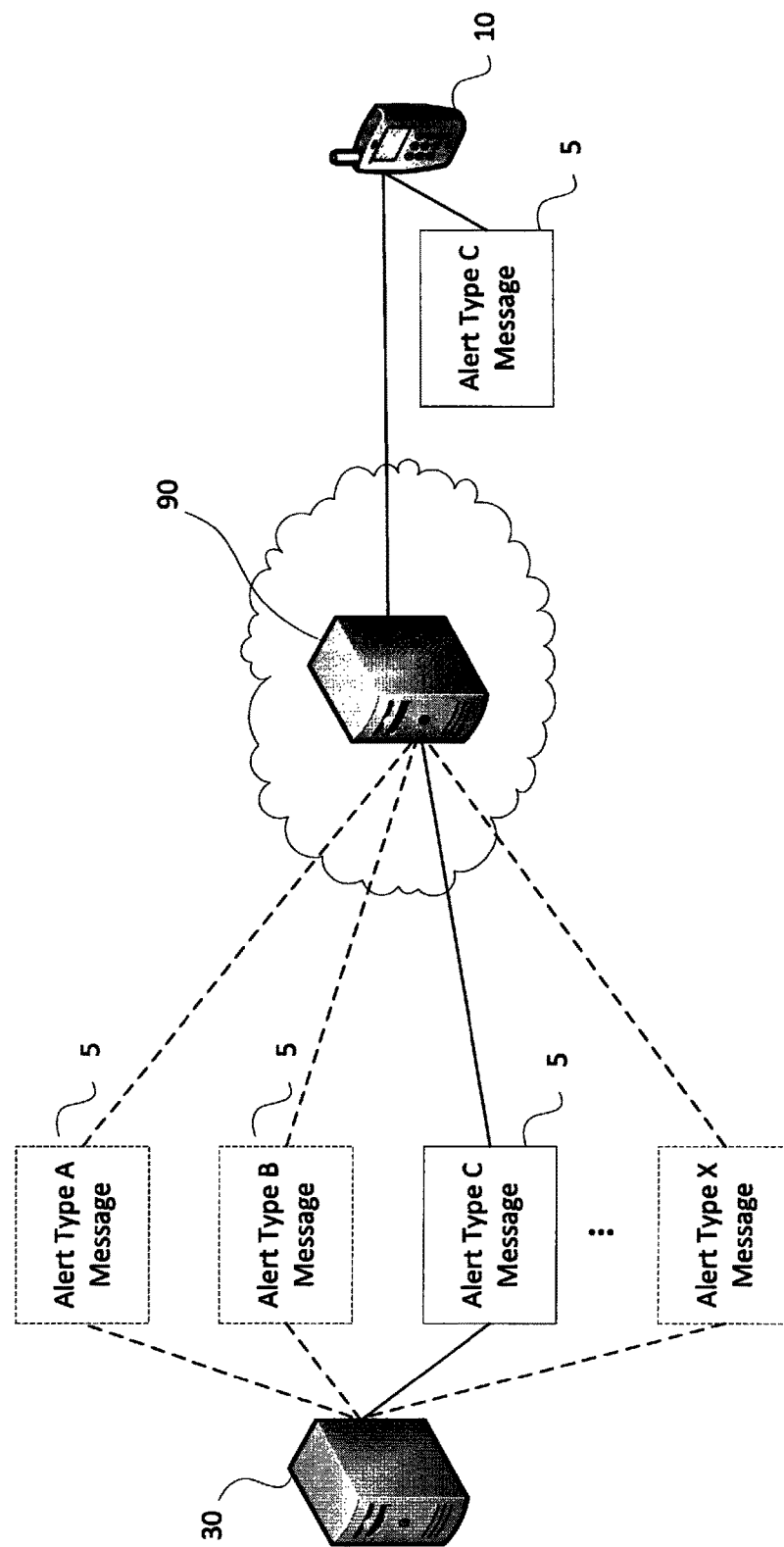
FIG. 3 is a diagram of an example configuration sending a message to a destination device triggering a specific alert.

With reference to FIG. 3, an example configuration shows sending the message 5 to the receiving device 10 triggering a specific alert. The messages are sent from a single one of the physical sending stations 30, but differentiate message content by the alert. Alerts may be grouped, but specific patterns indicate different nature, urgency, and/or expected response.

For example, a radiology image for a patient having a broken limb may show an alert pattern which is a yellow light indicating the image is present, and a non-life threatening surgery will need to be scheduled. A radiology image for a patient scheduled for emergency surgery with a life threatening condition may show a flashing red light. If the surgery is imminent or review of the image is necessary to determine aspects of the emergency surgery, then an audible alert may be added. Radiology is the same source for all of the messages in this example, but the message content is differentiated by the alert pattern.

The alerts may be specific to a specialty. A family medicine practitioner may use different alerts from a surgeon or an internal medicine practitioner. For example, an alert from a practitioner's office may use one ringtone for message that indicates medication request for patient in pain versus a different ringtone for message from the office regarding a scheduling problem. The expected response is different. In the first instance, the practitioner reviews the message and orders a prescription. In the second instance, a call to the scheduler at a later time may be warranted. The different alerts for each of multiple messages allow the practitioner to address several messages with one call or system use.

In another example, the system alerts for an ICU practitioner differentiate the criticality of the message. One ringtone may indicate a malfunction of a device, while a different ringtone indicates a suspicious abnormal patient condition recorded by the monitor, while another ringtone denotes life threatening conditions have been/are being monitored. These indications may call for actions with different degress of immediacy. The first may suggest that a call should be made to arrange for a back-up device. The alert with the ringtone from an event associated with a patient in one bed versus the ringtone from an event associated with a patient in another bed may indicate a different urgency of response depending upon the condition of the patient.

Protocols properly configured allow association of ringtone patterns, vibration patterns, and/or light patterns. The source using a sending station 30 can be differentiated using PSTN numbers (caller ID) of the messages 5, the SIP registered logical source address, the source IP addresses and/or port numbers, the destination IP address and/or port numbers, and the SIP registered destination logical address.

With reference to FIGS. 4A-C, the message content can be identified in a variety of alternative ways. The configuration of the particular device 10 establishes how each alert is determined and how it is manifested on the particular device. The alert can be indicated in the logical address 410 of an originator or source. Alternatively, the alert can be indicated in the logical destination address 420. The SIP registration command permits use of logical addresses and resolves a logical address to an actual address. The receipt of the message 5 by the device 10 uses one or both of the logical addresses to trigger the alert configured on the device 10.

Another embodiment uses an application installed on the practitioner's receiving device 10 to inspect the message body. As the message is received, the application opens the body of the message 430 and inspects a designated portion, such as the initial portion for an alert indicator. The message can be voice, text, or the like with an encoding which specifies the alert. For example with voice messages, the application can search for a voice command. An example of a voice indicator can be "code blue," etc. using colors or other standardized methods frequently used in hospitals.

With reference to FIG. 5, an example table shows alert 500 configurations manifested at a destination device 10. The alerts can be only ringtones 510. The alerts can also be vibrations 520 or light displays 530 using a display screen of the receiving device. The alerts can be combination of ringtones, vibration patterns or lighting patterns. How each alert is manifested is determined by a configured of a device 10. Each alert can be associated with an expected action 540 to be taken by the healthcare practitioner.

The light display alerts 530 are perhaps the least intrusive. A particular color can be displayed on the display screen of the device. The color can also be made to turn on and off in a particular pattern. The light display provides a visual indication to a healthcare practitioner which may not be visible to a patient or may easily viewed as a situation permits when carried on a person. However, in order to see the display, the display must be visible to the healthcare practitioner.

The vibration pattern alerts 520 are felt by a person carrying a device. Vibration patterns used in alerts can be continuous or intermittent. Vibrations can be varied in intensity, speed, and time on, and time off and the like to differentiate between alert levels. Ringtone patterns 510 are well known in the industry and can include audible patterns and/or recordings. Customizable recordings are also used. Depending upon the ringtone selected, the ringtone may be more or less intrusive as needed.

The alerts 500 can be grouped to indicate the nature, urgency or expected response. This allows the healthcare practitioner to use standardized message content groups, with alerts which are meaningful. The level of importance may be differentiated in the alerts using the light, vibration, ringtone patterns or the like. Even informational messages such as confirming appointment, confirming discharge, insurance payment received, or arrival of scheduled patient can trigger different responses which impact service, yet can be accomplished with alerts.

For example, the alerts 500 can indicate a timeframe for a response. One alert may indicate immediate action. Yet another alert may indicate that action is requested within an hour. Another may indicate that action is requested by the end of the day. The alert 500 can indicate to whom a response is to be sent such as an office, radiology, lab, ICU, EMR, etc. The alert 500 can indicate about whom the message concerns such as in-patient, outpatient, administrative, or personal. The alert 500 can indicate the type of action or response such as call the source, email the source, text the source, review the message and decide, or go to a specific location, etc.

With reference to FIG. 6, an embodiment with a 1-n mapping of device destinations and an m-1 mapping of sources is illustrated using the SIP protocol server 80. This embodiment uses the 1-n and m-1 mappings separately or in combination with other configurations. The 1-n mapping of device destinations uses a forking of SIP or the forward capabilities of the Internet Protocol to send a message 5 to multiple devices 10 where all the messages are sent to one destination 600. The healthcare practitioner 20 may use a phone, smartphone, a tablet, other computing device with connectivity, combinations or multiples. The 1-n mapping allows messages to be sent to all devices, each device, or combinations of the devices 10. The 1-n mapping is be done by a SIP server 90 using forking proxies or by an IP server with multiple forwarding destinations. The SIP server offers the most flexibility. The IP server typically requires a browser session to enter and establish a forwarding list.

The m-1 mapping shows how multiple destination addresses 610 are mapped to a single one of the devices 10. Using the SIP proxy server 90, multiple logical destinations are registered to the single device. Each address represents a different message category or alert type. For example, address B, C, and D are used for the destination associated with an alert groups 1, 2, and 3 respectively. The alert level of the message is reflected by which logical destination address is used. Addresses from different domains may be registered to map to the same device.

In another embodiment, the 1-n and m-1 mappings are used in combination. A healthcare practitioner may receive messages and associated alerts from multiple sources, sent to multiple logical destinations, and all be received by one or several destination devices which trigger an alert based on the message content.

With reference to FIG. 7, a flowchart shows an embodiment which reads the content of a message body to determine the type of alert. An application is installed on the device 10 in step 700. In a step 710, the application waits for a message 5 to arrive. The application may be configured to wait for a specific source and/or destination address or may review all messages. In step 720, the application reads a designated portion of the message body for a code indicative of the type of alert. The alert of a specific type is triggered in step 730 which can include a light pattern, a vibration pattern, and/or a ringtone pattern. The alert pattern differentiates the message content to a clinician 740.

With reference to FIG. 8, a flowchart shows an embodiment which triggers alerts based on the message content reflected by the source and/or destination address. The device 10 is configured in a step 800 to associate each source and/or destination address with specific one of the alert patterns 500. The device 10 waits at a step 810 for a message to be received. Once the message has been received, the message content and the type of alert are determined in a step 820 by the configuration of source and/or destination addresses or numbers. The corresponding alert 500 is determined such as the ringtone pattern, the vibration pattern, the light pattern, or a combination thereof. The alert determined by determination in the step 820 is played in a step 830. In a step 840, the practitioner interprets the type of alert from the configuration of the step 810 and the alert pattern from combinations of ringtones, light patterns, and vibration patterns performed by the device 10 to indicate the action to be taken.

With reference to FIGS. 9A and 9B, the set-up and sending of messages in one embodiment are shown respectively. In a step 900 of FIG. 9A, alert categories are defined. The categories represent message content such that the nature, urgency, and expected action are common for a message category. The message categories represent the agreed upon action expected of the practitioner 40 by the healthcare facility 25. The message categories can be based on healthcare protocols, healthcare service provider protocols, or healthcare facility protocols and can be specific to each healthcare practitioner. In a step 910, the healthcare facility configures the source addresses 410 according to the defined alert categories. Configuring source addresses can include reserving PSTN numbers, IP addresses and/or port numbers, SIP addresses and/or port numbers. Configuring source addresses can also include registration of addresses with the SIP server 90 or an IP server.

In a step 920, optionally the healthcare facility or service provider can register addresses and/or reserve numbers for each practitioner to include specific destinations 420 or permit multiple device mappings 600. The step 920 can be used to customize settings for each practitioner or can be used as a generalized practice for practitioner driven alerts.

In an alternative embodiment, if alerts are encoded in the message body 430, then set-up in the steps 910 and 920 is reduced.

The messages are encoded in a step 930. The encoding includes selecting the specific source 410 and/or destination 420 for the message which indicates the nature, urgency, or expected response for the message being sent. The sending station performs the encoding as part of sending the message. In alternative embodiment, the alert category is included as part of the message. The alert category can be entered text or entered voice commands or inferred natural language, key words, or the like which are interpreted on the receiving device 10. The message 5 is sent by the sending station 30 in a step 940.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system for alerting healthcare practitioners comprising:
    a plurality of receiving devices, each receiving device associated with a corresponding healthcare practitioner including:
        an user alerting device which alerts the practitioner to a received message with one of a plurality of types of alerts;
        a receiver which receives the incoming messages; and
        circuitry which causes the user alerting device to alert the practitioner to an incoming message with one of the plurality of types of alerts; and
    a sending station which sends the messages carrying healthcare information of one of a plurality of preselected types of healthcare significances to a selected one or more of the receiving devices, each message corresponding to a selected one of the types of alerts, such that the receiving device alerts the practitioner to receiving the message with the selected type of alerts; and
    wherein the sending station includes:
        a plurality of sending station identifiers, each identifier corresponding to one of the types of alerts, the message being sent with one of the sending stations corresponding to a selected alert such that the alerting device responds to the sending station identifier with the selected alert; or
    wherein at least one of the receiving device includes:
        a plurality of receiving station identifiers, each identifier corresponding to one of the types of alerts, the sending station sending the message to a receiving station identity corresponding to a selected alert such that the alerting device responds to the receiving station identifier with the selected alert.

2. The system for alerting healthcare practitioners according to claim 1, further including:
a patient monitor which monitors physiological parameters, the monitor outputting a message to one of the practitioners indicative of the monitored physiological conditions in response to each of a plurality of selected medical criteria, the sending station associating the selected medical criteria of each message with a corresponding type of alert and sends the message to the one of the practitioners, such that the receiving device associated with the practitioner alerts the practitioner with the type of alert which corresponds to the healthcare significance of the message.

3. The system for alerting healthcare practitioners according to claim 1, wherein the sending station encodes an alert type into the message and the receiving device circuitry reads the messages and decodes the encoded alert.

4. The system for alerting healthcare practitioners according to claim 1, wherein at least one of the user alerting devices includes at least one of:
an audio output device, a vibrating device, and an optical output device.

5. The system for alerting healthcare practitioners according to claim 1, wherein a ringtone of an audio output device, a vibration pattern of vibrating device, or a pattern or a color of light by an optical output device indicates the type of alert.

6. The system for alerting healthcare practitioners according to claim 1, wherein at least one of the sending station identifier and the receiving station identifier is at least one of:
a source Public Switched Telephone Network (PSTN) number;
a source IP address;
a source IP port number;
a SIP registered source logical address;
a destination IP address;
a destination IP port number, and
a SIP registered destination logical address.

7. The system for alerting healthcare practitioners according to claim 1, further comprising:
a Session Initiation Protocol (SIP) configured server which acts as a proxy server to direct messages which include one or more logical addresses to one or more physical receiving devices.

8. The system for alerting healthcare practitioners according to claim 1, wherein:
the sending station includes a plurality of sending station identifiers, each identifier corresponding to one of the types of alerts, the message being sent with one of the sending stations corresponding to a selected alert such that the alerting device responds to the sending station identifier with the selected alert; and
a ringtone of an audio output device, a vibration pattern of a vibrating device, or a pattern or a color of light by an optical output device indicates the type of alert.

9. The system for alerting healthcare practitioners according to claim 1, wherein:
at least one of the receiving device includes a plurality of receiving station identifiers, each identifier corresponding to one of the types of alerts, the sending station sending the message to a receiving station identity corresponding to a selected alert such that the alerting device responds to the receiving station identifier with the selected alert; and
a ringtone of an audio output device, a vibration pattern of a vibrating device, or a pattern or a color of light by an optical output device indicates the type of alert.

10. A system for alerting healthcare practitioners comprising:
a patient monitor which monitors physiological parameters, the monitor outputting a message to one of the practitioners indicative of the monitored physiological condition and a healthcare significance of the monitored physiological condition; and
a sending station which associates an alert type which corresponds to the healthcare significance associated with the message and sends the message and the associated alert to a receiving device of the one of the practitioners such that the receiving device associated with the practitioner alerts the practitioner with the type of alert which corresponds to the healthcare significance of the message; and
wherein the sending station includes:
a plurality of sending station identifiers, each identifier corresponding to one of the types of alerts, the message being sent with one of the sending stations corresponding to a selected alert such that the alerting device responds to the sending station identifier with the selected alert; or
wherein the receiving device includes:
a plurality of receiving station identifiers, each identifier corresponding to one of the types of alerts, the sending station sending the message to a receiving station identity corresponding to a selected alert such that the alerting device responds to the receiving station identifier with the selected alert.

11. A method for alerting healthcare practitioners comprising:
sending a message to a receiving device, the message carrying healthcare information with one or a plurality of types of preselected health care significances;
with the receiving device, receiving the healthcare message and responding to receipt of the message by performing a type of alert corresponding to the one of the types of healthcare significances of the message carried healthcare information; and
wherein the method further comprises:
encoding the message to be sent using one of a plurality of sending station identifiers, each identifier corresponding to one of the types of alerts, such that the receiving device responds with the alert corresponding to the sending station identifier; or
encoding the message to be sent using one of a plurality of receiving station identifiers, each identifier corresponding to one of the types of alerts, such that the receiving device responds with the alert corresponding to the receiving station identifier.

12. The method for alerting healthcare practitioners according to claim 11, further comprising:
outputting the message to be sent with a patient monitor which monitors physiological parameters to one of the practitioners indicative of the monitored physiological conditions in response to each of a plurality of selected medical criteria.

13. The method for alerting healthcare practitioners according to claim 11, further including:
encoding an alert type into the message with a sending station; and reading the message at the receiving device and decoding the alert.

14. The method for alerting healthcare practitioners according to claim 11, wherein encoding the alert type includes insertion of text or voice commands into the message body indicative of the alert type.

15. The method for alerting healthcare practitioners according to claim 11, wherein performing the alert type includes at least one of:
   playing a pre-determined ringtone on the receiving device;
   vibrating the receiving device according to a pre-determined pattern; and
   displaying a pre-determined pattern of light or a color of light on an optical output device of the receiving device.

16. The method for alerting healthcare practitioners according to claim 11, wherein the sent message includes at least one of:
   a source Public Switched Telephone Network (PSTN) number;
   a source IP address;
   a source IP port number;
   a SIP registered source logical address;
   a destination IP address;
   a destination IP port number; and
   a SIP registered destination logical address.

17. The method for alerting healthcare practitioners according to claim 11, wherein the message includes at least one of:
   a voice message;
   a SMS message;
   an email message; and
   an instant message (IM).

18. A method for alerting comprising:
   sending a message to a selected one or more receiving devices, the message carrying information corresponding to one or a plurality of types of preselected significances;
   with one of the receiving devices, receiving the message and responding to the receipt of the message by performing a type of alert corresponding to the one of the types of preselected significances; and
   wherein an alert corresponding to the one of the types of preselected significances includes an indication that a response is to be sent to at least one of an office or a lab; and
   wherein an alert is indicated in either a logical address of a sending device or a logical destination address.

19. The method of claim 18, wherein the alert is indicated in the logical address of the sending device.

20. The method of claim 18, wherein the alert is indicated in the logical destination address.

* * * * *